(12) United States Patent
Patra et al.

(10) Patent No.: US 6,831,214 B2
(45) Date of Patent: Dec. 14, 2004

(54) **VAISHNAVI, A HIGH YIELDING SELF-POLLINATED *CYMBOPOGON MARTINII***

(75) Inventors: Nirmal Kumar Patra, Lucknow (IN); Sushil Kumar, Lucknow (IN); Alok Kalra, Lucknow (IN); Herikesh Bahadur Singh, Lucknow (IN); Hemendra Pratap Singh, Lucknow (IN); Ved Ram Singh, Lucknow (IN); Hasan Tanveer, Lucknow (IN); Nareshwar Mengi, Lucknow (IN); Om Parkash Dhawan, Lucknow (IN); Mahendra Singh Negi, Lucknow (IN); Paltoo Ram, Lucknow (IN); Vijay Pal Singh, Lucknow (IN); Jitendra Pal Singh, Lucknow (IN)

(73) Assignee: Council of Scientific & Industrial Research, New Delhi (IN)

( * ) Notice: Subject to any disclaimer, the term of this patent is extended or adjusted under 35 U.S.C. 154(b) by 0 days.

(21) Appl. No.: 10/331,010

(22) Filed: Dec. 26, 2002

(65) Prior Publication Data

US 2003/0154520 A1 Aug. 14, 2003

Related U.S. Application Data

(63) Continuation of application No. 09/666,876, filed on Sep. 20, 2000, now abandoned.

(51) Int. Cl.$^7$ ............................ A01H 5/00; A01H 1/00; A01H 1/02
(52) U.S. Cl. ......................... 800/320; 800/298; 800/260
(58) Field of Search ................................. 800/320, 298, 800/260; PLT/388, 384

(56) References Cited

PUBLICATIONS

Singh et al., "Identification Of Resistant and Susceptible Alleles For Reaction To The Rust (Puccinia Nakanishikii) In Lemongrass (*Cymbopogon flexuosus*)"; *Journal of Medicinal and Aromatic Plant Sciences*, 21, 1999, (pp. 695–699).

*Primary Examiner*—Kent Bell
(74) *Attorney, Agent, or Firm*—Christie, Parker & Hale, LLP

(57) ABSTRACT

The invention relates to a novel palmarosa plant christened as "Vaishnavi", said plant capable of setting seeds under selfing conditions and having high oil yield potential, and developed employing crop-burning technique as a physical mutagen.

2 Claims, 5 Drawing Sheets

Figure 1A:
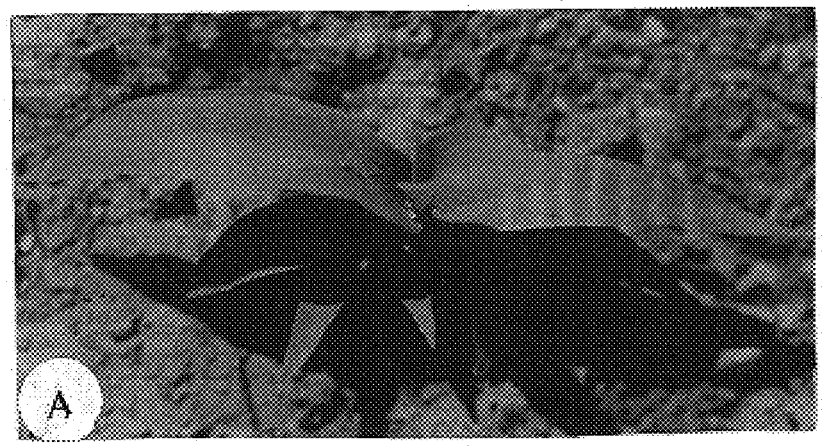

(5 of 5 Drawing Sheet(s) Filed in Color)

VAISHNAVI, A HIGH YIELDING SELF-POLLINATED CYMBOPOGON MARTINII

CROSS-REFERENCE TO RELATED APPLICATION

The present application is a continuation of U.S. application Ser. No. 09/666,876, filed Sep. 20, 2000, now abandoned, the entire disclosure of which is expressly incorporated herein by reference.

FIELD OF INVENTION

The present invention relates to a self-pollinated genotype of *Cymbopogon martinii* christened as "Vaishnavi" and belonging to the family Gramineae. The plant "Vaishnavi" has been bred using the selfing system without causing inbreeding depression as against all existing palmarosa genotypes with almost no selfing but crossing system providing thereby a foundation for the long sought systematic plant breeding in palmarosa via deployment of scheme for introducing desirable gene(s) from diverse sources into "Vaishnavi" and fixing the introduced genes through simple selfings and progeny selections.

BACKGROUND OF THE INVENTION

Essential oil bearing perennial grasses of India belong to the tribe Andropogoneae of which Cymbopogon forms an important genus comprising 140 species amongst which palmarosa (*C. martinii*) merits special importance being so far known as the major source of geraniol ($C_{10}H_8O$), an unsaturated primary terpene alcohol, the most widely used chemical in perfume industries. Although palmarosa, owing to its industrial importance, is grown world wide and has been given suitable emphasis for its genetic improvement, breeders' efforts in the latter aspect have not as yet witnessed impressive success in developing high yielding varieties. Indeed, genetic improvement in palmarosa is very difficult primarily due to lack of scope for controlling its mating system. This is usually a cross-pollinated crop having very small tendency for setting seeds under selfing conditions. Further, very small size of florets in this crop greatly impedes manual emasculation and pollination. Thus, seed setting under controlled selfing and crossing based on testing are not feasible in palmarosa (Srivastava and Tyagi 1986; Patra and Sharma 1989; Patra et al. 1997; Patra and Kumar 1999). Although population improvement approach has repeatedly been resorted to earlier, not even a single variety till date is available, which would offer a guarantee for its sustained advancement in oil productivity as well as oil quality. Seed contamination from wild sources or, seed heterogeneity often caused by nonrandom mating among individuals within the population of a population cultivar leading to frequent deviations in oil productivity and quality are the general in features this out-breeding species. Keeping these limitations of the crop in view, planned efforts were made by the Applicants to explore the possibility of obtaining via extensive individual plant and half-sib family selections, a genotype with high oil yield potential and large tendency for seed setting or a half-sib genotype having much impressive oil yield potential coupled with ability to sustain homogeneity in its out-crossing population.

OBJECTS OF THE INVENTION

The main object of invention is to develop a novel palmarosa genotype via deployment of half-sib family selection with capacity to set large number of seeds under selfing conditions and having high oil yield potential.

Another object of invention is to ascertain the effect of high temperature of crop-burning practice for weed control, on the normal growth morphology, productivity and quality of the crop (palmarosa).

A further object of invention is to develop a novel palmarosa plant producing oil with high amount of geraniol.
s

SUMMARY OF THE INVENTION

Figure 2A:
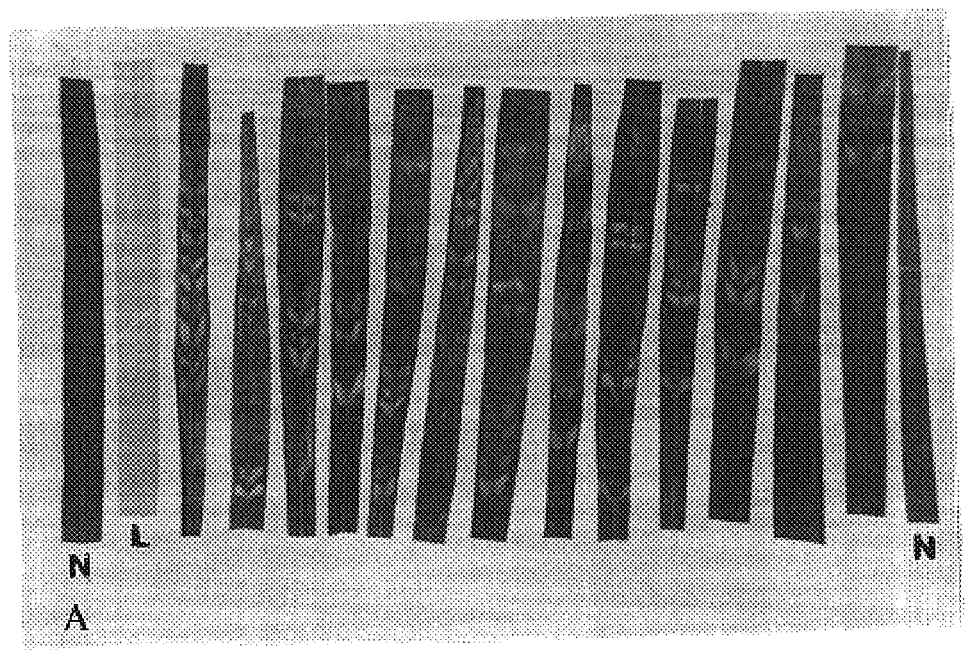

Half-sib family selections aimed at developing high yielding genotypes with high potential for setting seeds under selfing conditions were exercised in an old plant population the large part of which was got free of weeds and unwanted dry crop stubbles by deploying the "burning technique", generally applied to crops like palmarosa and sugarcane by the North Indian farmers. Flood irrigation was immediately given to the superficially burnt plants for the purpose of their survival and regeneration. Attempts were made to collect seeds from controlled selfings and open pollinations in burnt as well as unburned (normal) plants. None of the individuals in both cases of plants showed viable seeds under controlled selfing conditions. Viable seeds could be collected only from open pollinated plants. The absence of seed setting under selfing led to refer the open pollinated seeds of known mother plants as the "seeds from natural half-sib mating". Seeds (half-sibs) of selected plants that are burnt and those that are not burnt were grown in a nursery and subsequently, the nursery seedlings were transplanted in blocks as half-sib families ($S_0$ families). Seeds of the selected $S_0$ plants were separated, collected and $S_1$ populations were raised in the same way as done for $S_0$ population. Whereas $S_0$ plants of both types were normal looking with almost similar morphology, deviations in result in this regard were recorded in $S_1$ generation (equivalent to $F_2$ generation of normal plant crosses) for the burnt class of plants for three counts. First, among the 100, $S_1$ half-sib families, 15 exhibited chlorophyll with frequency ranging between 0.6 to 7.8%. All the chlorophyll variants, with rare exceptions, were identical, all occurring in the form of "Zebra cuts" as shown in FIG. 2A. None of the control (unburned half-sib) families reveal chlorophyll variation. Second, the burnt material in general, exhibited doubled somatic reproducibility in terms of tillering ability (30 to 70 tillers/plant against 15–20 Of the control). Third, the $S_1$ family having maximum frequency of (7.8%) chlorophyll variants exhibited unique macro-variants with flower structure of self-pollinated plants like wheat and rice. This exceptional variant was multiplied by selfed seeds, characterized for its morpho-physiological plant attributes including oil content and productivity and was named as "Vaishnavi". This unique genotype, despite its selfing, does not exhibit inbreeding depression. Vaishnavi, with all its plant-characters firmly fixed, highly excels all other existing genotypes for oil productivity. Inheritance study revealed that Vaishnavi is recessive homozygous for all its morphological traits which transmit all its traits en block from one generation to the next. Results of half-sib families of the burnt class of original plants and further experiment over the effect of superficial crop-burning temperature, convincingly raised the possibility that Vaishnavi as well as the chlorophyll variants derived their origins due to mutations induced in their progenitor (mother) plants by the high temperature of superficial crop-burning. Accordingly, high temperature from crop-burning has been suggested as a potent mutagen for inducing mutations in hardy grass crops like palmarosa.

BRIEF DESCRIPTION OF THE ACCOMPANYING DRAWINGS

The file of this patent contains at least one drawing executed in color. Copies of this patent with color drawing (s) will be provided by the Patent and Trademark office upon request and payment of the necessary fee.

FIGS. 1A–1G describe Morpho-cytology of the new variety Vaishnavi and chlorophyll variant (*Cymbopogon martinii*) as follows:

FIG. 1A describes chlorophyll variation as "Zebra-cuts" (FIG. 2A) at the $6^{th}$ leaf-stage of superficially burnt progenitor of PRC-1.

Figure 1B:
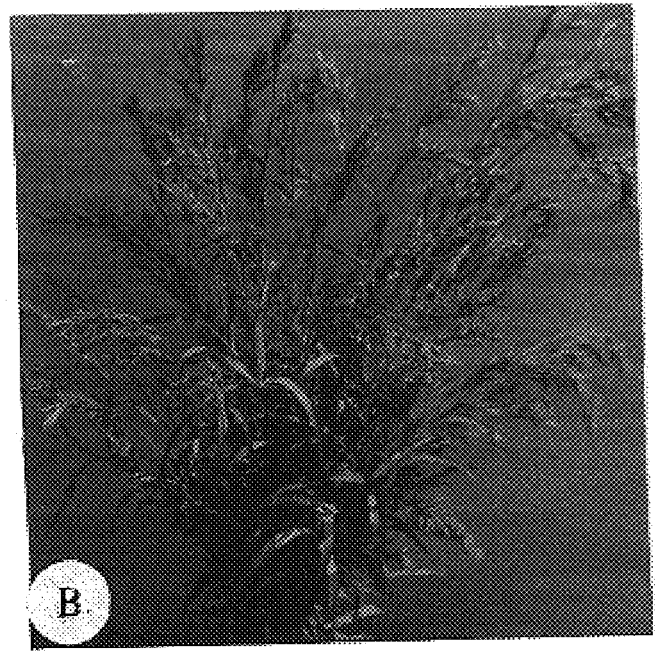
Figure 1C:
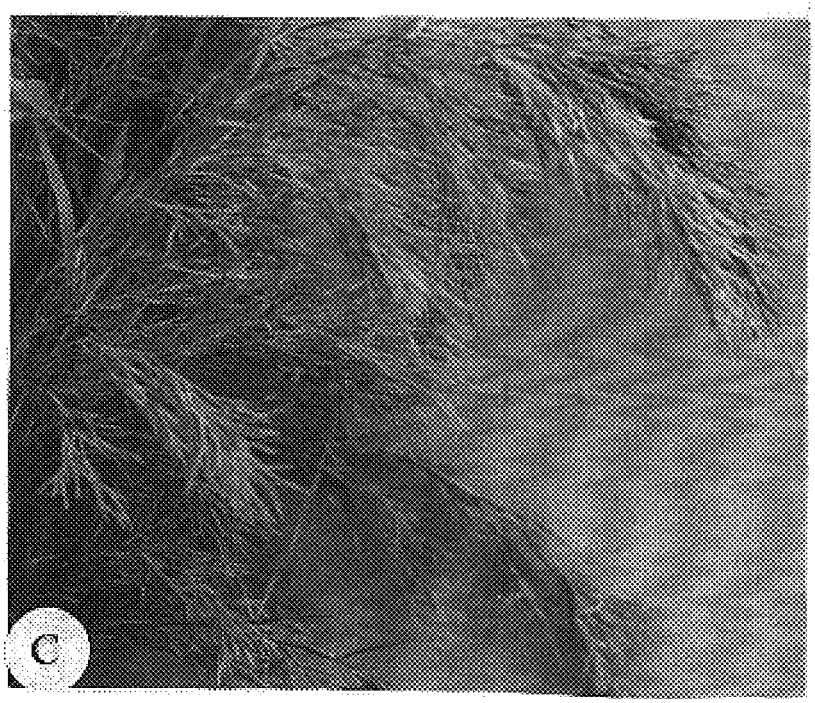

FIGS. 1B and 1C describe self pollinated Vaishnavi matured plant and young plant, respectively; mark the robust inflorescence.

Figure 1D:
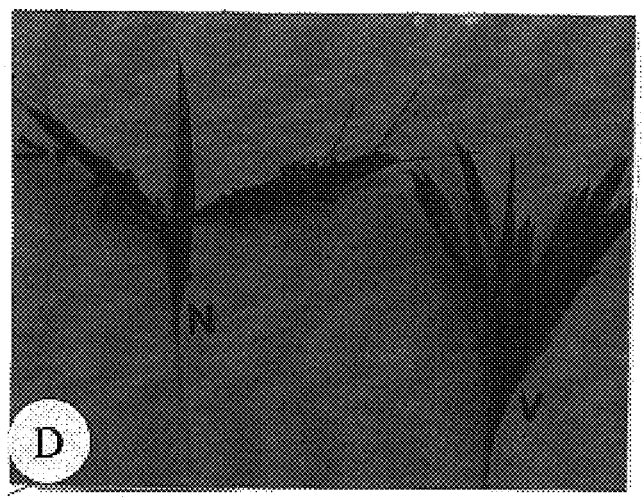

FIG. 1D describe Spikelets of the normal cross-pollinated plant (PRC-1) (marked as "N") and self pollinated plant Vaishnavi ("V"); Mark the distinct feathery stigmas coming out of the awned florets of the spikelet during anthesis of normal plants (marked with arrow) and shy stigmas remaining in side the awnless florets (cleistogamy) of Vaishnavi.

Figure 1E:

FIG. 1E describes normal tall statured cross-pollinated plant (grown to maturity).

Figure 1F:
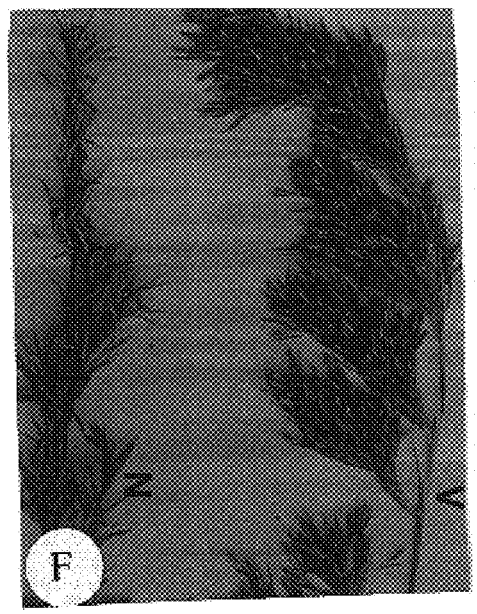

FIG. 1F describes inflorescence of Vaishnavi ("V") and normal plant ("N").

Figure 1G:
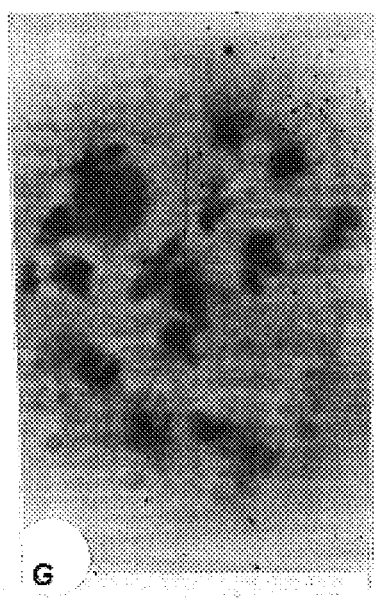

FIG. 1G describes a pollen mother cell of Vaishnavi of the diakinesis stage of meiosis exhibiting the normal chromosome number 2n=2x=20 (10 bivalents).

FIGS. 2A–2E describe variations induced by crop-burning in Vaishnavi (*Cymbopogon martinii*) as follows:

FIG. 2A describes chlorophyll variations largely as "Zebra-cuts".

Figure 2B:
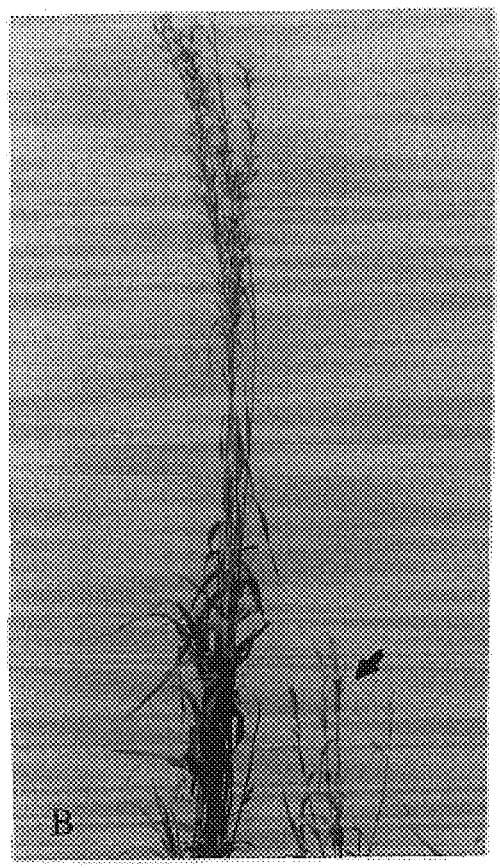

FIG. 2B describes viable extra-tall and lethal extra-dwarf (lethal albino) variant.

Figure 2C:
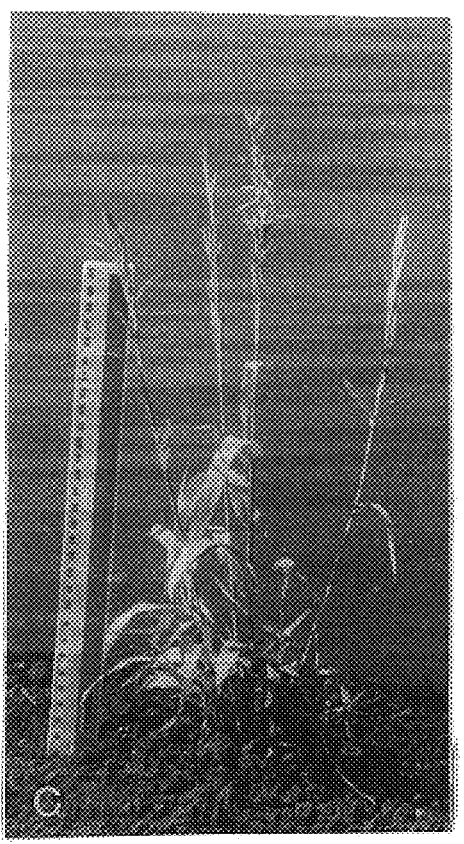

FIG. 2C describes close-up of lethal albino variant.

Figure 2D:
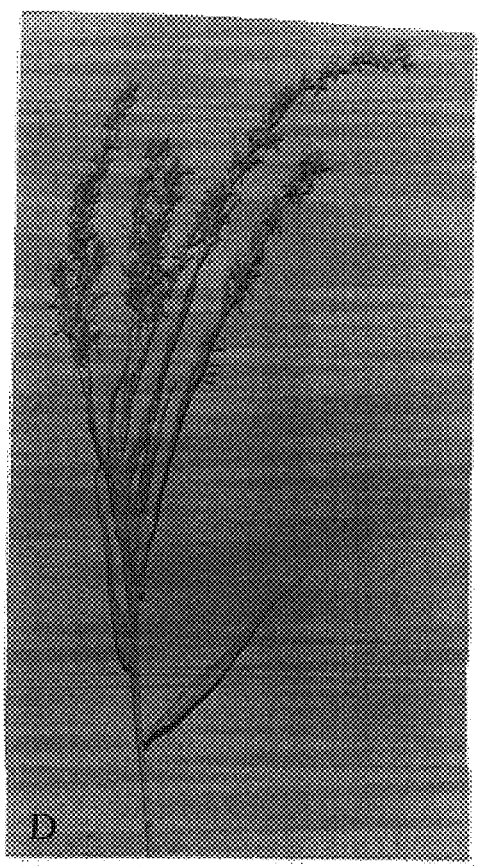

FIG. 2D describes a variant with multi-branched inflorescence.

Figure 2E:

FIG. 2E describes a dwarf variant with much up-graded morphological fitness.

DETAILED DESCRIPTION

Breeding History:

The high yielding self pollinated genotype "Vaishnavi" developed by the Applicants is an out-come of a strategic approach of selecting the mother plants (the original gene pool for the experiment) with high per se oil content and high selfed seed yield, assessing progenies of the selected plants, raising true-bred (homozygous) progeny lines via repeated selfing of the selected plants and assessing the top ranking progeny true-bred (fixed) for all plant traits against standard varieties.

Accordingly, the present invention provides a high yielding, stable and self-pollinated plant *Cymbopogon martinii* christened as Vaishnavi, belonging to the family Graminae (Poaceae) and having the following characteristics a. Self-pollinated genotype having no inbreeding depression;
b. possessing cleistogamous habit only for stigma (shy stigma) that does not come out of glumes of the florets and hence preventing out-crossing;
c. containing robust inflorescence having maximum oil concentration
d. florets ranging between 1780 to 1840 arranged in clusters on rachis;
e. recessive homozygous (true-bred) for all its morpho-physiological traits transmitting the said traits en block from its one generation to the next generation without undergoing genetic recombination between traits;
f. inflorescence: stem (w/w) ratio ranging between 1.40 to 1.50 wherein robust inflorescence having the maximum oil concentration
g. oil content ranging between 0.75 to 0.80%;
h. seed yield of at least 24.3 quintals per hectare;
i. oil yield of at least 164.7 kg per hectare;
j. geraniol yield of at least 135.0 kg per hectare
k. oil constituents comprising maximum extent of geraniol of at least 78% and geranyl acetate of at least 8% and the rest being unidentified fractions in the essential oil all totaling to 100% at different stages of growth.

The invention further provides a method for obtaining self-pollinated genotype 'Vaishnavi' which comprises:

(a) burning basal hardy stem part of at least 2 years old field-grown plant for about 1–2 minutes during winter season having the maximum day temperature ranging between 25°–38° C.;
(b) flood irrigation of the superficially burnt plants within a day of completion of burning;
(c) employing suitable interculture practices and manuring for the surviving plants forming $M_1$ population for ensuring their proper growth and rejuvenation.
(d) selecting normal looking plants from $M_1$ population and taking them out of the original field for raising their clonal population during rainy season in isolated blocks by using their vegetative slips;
(e) employing open-pollinations within the selected clones of $M_1$ population from step (d) above for raising their seeds ($M_2$s) through natural full-sib matings.
(f) growing the seeds ($M_2$s) drawn in bulk from the $M_1$ clones to flowering as $M_2$ plants and studying their macro- and micro-variations induced by the high temperature of crop burning;
(g) generating $M_3$ population from $M_2$ mutant plants in the same way as done for advancing $M_1$ population to $M_2$ population for raising homozygous $M_3$ lines;
(h) multiplying desirable true-bred mutant(s) through their seeds from full-sib matings.

High temperature from superficial crop burning is to be used as a potent physical mutagen only for the hardy grassy crop selected from palmarosa and sugarcane.

Seeds which are cultivar 'Vaishnavi' are deposited with the National Collections of Industrial, Food and Marine Bacteria (NCIMB), 23 St. Machar Drive, Aberdeen, AB24 3RY Scotland, United Kingdom (Seed Deposit Accession No. NCIMB 41154). 2500 seeds were deposited with NCIMB on Jan. 21, 2003 under the Budapest Treaty.

The seeds of the mother plant PRC-1 have been deposited at the Central Institute of Medicinal, Aromatic Plants, Lucknow, India bearing the accession no. CIMAP/0616.

During the course of genetic improvement in the cross-pollinated crop: palmarosa (*Cymbopogon martinii*) via deployment of half-sib family selection scheme at Central Institute of Medicinal and Aromatic Plants, Lucknow, India, unusual genetic variations were marked in the half-sibs, raised from the seeds of plants surviving after superficial "burning" which is generally given by crop growers to the old and hardy plantations of palmarosa and sugarcane to make them free from weeds and unwanted crop-debris. Among the obtained variants (chlorophyll and other visible variants), one named as "Vaishnavi" was most unusual in view of its floral structure of conventional self-pollinated crops like wheat and rice and ability of sustaining supremacy in productivity without undergoing inbreeding depression for its morpho-physiological attributes. The invention of "Vaishnavi" (the first self-pollinated genotype of palmarosa) in turn, led to further experiment on the effect of exposing palmarosa plants to high temperature of crop-weed burning; the obtained results convincingly raised the possibility that the high temperature from crop stubbles and weeds burning may be a potent physical mutagen for including heritable variations ("mutations") in the high temperature tolerant crop like old palmarosa plants.

Among the existing palmarosa varieties, PRC-1 earlier developed by this Institute is most familiar for its oil productivity as well as open pollinated seed yield. This variety was identified as the starting genetic material for exercising selections. The Applicants selected a well grown three years old PRC-1 plantation comprising 20,000 plants, each having space of 60 cm×30 cm and all being accommodated within the total plantation area of ½ hectare. In order to get the plantation free from weeds as well as undesirable dry crop-stubbles (dry tillers) associated with the other wise living clumps of healthy tillers, the mentioned practice of crop burning was adopted during November, 1988 at CIMAP (Central-Institute of Medicinal & Aromatic Plants) Field Station, Pantnagar—i.e. after the Autumn crop harvesting had been over (only the aerial portion of plants containing leaves, hardy stems and inflorescences is harvested in this crop). The dry weeds and crop stubbles, besides facilitating their own burning, superficially effected the burning of the living tillers of almost all clumps. While initiating burning the Applicants took special care to leave one complete block having 5000 plants, as unburned control material to have a rough idea about the effect of crop-burning on plant traits especially oil quality. Immediately after the burning had been over by 6 hours (each plant took 2 minutes to get their dry tillers burnt), the whole burnt plantation-block with 15000 plants and the adjacent control block with 5000 plants were provided a flood irrigation. The surviving clumps sprouted their new shoots (tillers) 7–10 days after burning. It was worth while to see that the plantation, despite being exposed to such created environmental stress and hostility, did not reveal lethality in its clumps beyond 5.0 percent. Further, provided with regular irrigations at seven days intervals and suitable interculture (irrigation, manuring and weeding), the surviving plants, besides fully rejuvenating their tillers, attained normal growth behaviour, quite comparable to that of the unburnt plants by 2 months after their burning. A total of 300 high ranking plants (200 from the burnt plantation and 100 from the control block) on the basis of their performances for various morpho-metric traits including the major ones, namely plant height, tiller number, inflorescence: stem weight ratio and oil content (%), was selected during peak flowering time of May, 1989. All the 300 selected plants were covered of their 50% of the total tillers by muslin cotton bags during bud-stage of the florets during October, 1989 leaving their rest (50%) tillers for open pollinations of the florets. Viable seeds could be collected only from the open pollinated inflorescences of the unbagged tillers; none of the 300 selected plants set viable seeds under controlled selfing conditions (seed viability was tested during June, 1990 by germination tests in glass petri dishes and seed germinations in nursery). Thus, the selection experiment for identifying genotype with selfing system was not successful in spite of achieving significant results for productivity aspects.

Therefore, the Applicants directed their sole efforts to population improvement programme, especially for the augmentation of oil yield via the scheme of half-sib family selections using the open pollinated seed progenies (half-sibs) only of 160 top ranking selected plants (100 from the burnt "selected class" and 60 from unburnt "selected control-class") (Because, there was no seed setting in the selected mother plants under control selfing, the derived open pollinated seed progenies were considered as the half-sibs). Half-sib progenies (So generation) were planted in isolated blocks during July, 1990 for the purpose of avoiding possible seed-contaminations and their seeds ($S_1$ generation equivalent to $F_2$ of normal crosses in higher plants) could be collected during June, 1991. The $S_1$ progenies, when grown in separate nursery blocks during July, and subsequently planted in field during October 1991 revealed unusual results for at least three counts. First, among the 100 $S_1$ half-sib families, each of at least 260 plants (range: 260 to 572 plants per family), fifteen exhibited chlorophyll variants with the frequency of 0.6 to 7.8%. It was amazing to record that all the chlorophyll variants, with rare exceptions, were of identical type, all occurring in the form of "Zebra-cuts" as shown in FIG. 2A. The control plants did not reveal any chlorophyll variations. Second, the burnt material in general, exhibited doubled somatic reproducibility in terms of tillering ability (30 to 70 in some variants against 15–25 of the control). Third, the $S_1$ family having the maximum frequency (7.8%) of chlorophyll variants exhibited a unique macro-variant with completely a new morphotype not ever recorded earlier in palmarosa. This exceptional variant first labeled as CBHS-54 (Crop-Burning Half-Sib54), and later christened as "Vaishnavi" was first multiplied by collecting its seeds from the open pollinated inflorescence during two successive seasons (June, 1992 and December, 1992 at CIMAP Field Station, Pantnagar).

Morpho-Physiological and Genetic Analysis:

During the years 1993–94 a total of 200 healthy plants of "Vaishnavi" were raised in a separate progeny block measuring 9 m×4 m in size, sufficient for accommodating the plants by providing 60 cm×30 cm spacing for each plant for the purpose of conducting its morpho-genetic analysis. The plants were grown to flowering during October, 1993 and among them 100 plants were properly bagged before flower anthesis at their bud stage by the help of muslin cloth bags provided with internal ring guards made by galvanized wires and fixed with separate bamboo sticks so as to ensure protection of the bagged plants against possible mechanical injuries from controlled selfing. The seeds were collected from the bagged plants following their maturity during December, dried in sunshine and subsequently tested of their germination against the open pollinated seeds of two control genotypes (Trishna and PRC-1) in petri dishes and field nursery. While the petri dish-experiment revealed >80% germination, the nursery grown seeds showed somewhat low germination (60 to 70%). Such self pollinated seed viability in "Vaishnavi", though at par with the open pollinated seed viability (OPSV) of PRC-1, was higher than that of OPSV of Trishna. Thus, it could be well ascertained that "Vaishnavi" is a self pollinated genotype endowed with the property of high seed setting under controlled selfing.

Nonetheless, what was axiomatically important is that "Vaishnavi", besides maintaining some parity with the three control genotypes (Trishna, PRC-1 and Pantnagar Local) for seed germination highly excelled them for per hectare seed yield, the corresponding data being 25 q against 6 to 8 q of the three control genotypes. (Table. 1). As revealed by the detailed analysis of morphological peculiarities in "Vaishnavi" vis-a-vis the three mentioned normal cross-pollinated genotypes, the presence of robust inflorescence, florets per inflorescence in 2–3 fold more in number than the normal, very shy feathery stigma not at all coming out of the spikelet-glumes and thus, preventing its out-crossing (i.e. cleistogamous habit of its florets as in conventional crop like wheat and rice), profuse viable pollen grain productivity of the otherwise normal anthers leading the claimed plant to be an ideal pollen parent for crossing purposes, high biomass and seed yield and high per se oil content potential and almost absence of spikelet awns in "Vaishnavi", very distinctly mark if from all the existing genotypes of palmarosa. The detailed morpho-physiological specificities of "Vaishnavi", examined, are as given blow:

progenies except two having the PRC-1 (normal)-morphotype, were alike in morphology to the parental ("Vaishnavi") type, indicating thereby that "Vaishnavi", with rare exceptions of allowing about 3% out-crossing, is normally scheduled for selfing. The two rare hybrids with PRC-1-morphology (phenotype) in the "Vaishnavi"

| | |
|---|---|
| 1. Tribe | Andropogoneae |
| 2. Genus | Cymbopogon |
| 3. Species | *Martinii* var. *motia* |
| 4. Family | Gramineae (Poaceae) |
| 5. Common name | Palmarosa/Rush grass |
| 6. Plant height | 230.50 ± 1.3 cm.(Somewhat dwarf compared to tl existing genotypes PRC-1, Trishna and Pantnagar Local |
| 7. Growth habit | Somewhat droopy due to high weight of tl inflorescence. |
| 8. Stem | Thin, round, hardy, initially erect but droopy aft flowering and terete (cylindrical); main axis developing lateral branches (tillers) from the basal buds. |
| 9. Leaves: | Leaf sheath covering the inter node partially, inner surface glabrous (smooth) and upper surface some what hairy, junction of leaf sheath and leaf blade containing the ligule, as in normal plants. |
| Leaf length | 30.60 cm |
| Leaf width | 1.80 cm against 1.58 to 1.64 of the mentioned normal varieties. |
| Leaf colour[1] | Light green (137C). |
| 10. Inflorescence | Robust in size with large number of spikelets arranged in clusters on the rachis, giving a shape distinct from the normal plants with thin inflorescence without clustering in spikelets. |
| No. of rachilla of rachis per inflorescence | 13 as against 6 to 7 of the normal genotypes. |
| No. of florets per spikelets | 7 against 3–5 of the normal genotypes |
| No. of florets per inflorescence | 1820 against 216 to 560 of the mentioned normal genotypes. |
| Length of spikelet | 3.1 cm against 3.2 to 3.5 of the normal genotypes. |
| Fresh weight of inflorescence | 7.1 gm against 5.0 to 5.3 gm of the normal genotypes. |
| 11. Florets | Sessile, bracteate , narmaphrodite, almost awnless |
| Stamens | Three in number, having slender filament. |
| Carpel | One in number, with very shy stigma (cleistogamous) no coming out of the floret leading to no cross pollination |
| 12. Inflorescence: Stem weight ratio | 1.46 against 0.84 to 0.98 of the mentioned normal genotypes. |
| 13. Oil content (%) | 0.80 against 0.50 to 0.60 of the mentioned normal genotypes. |
| 14. Total oil yield per plant | 6.10 gm against 1.5 to 3.5 gm of the normal genotypes. |
| 15. Seed yield per plant | 73.4 gm (selfed seed) against 16.3 to 22 gm (open pollinated seed) of the normal genotypes. |
| 16. Oil quality | |
| Geraniol content | 78 to 82% |
| Geranyl acetate | 8 to 10% |

[1](The colour code referred were is in accordance with the "RHS colour cart" published by the Royal Horticultural Society, 80 Vincent Square, London SWIP 2PE, 1995).

"Vaishnavi" was attempted for understanding the inheritance of its plant traits and its degree of natural out-crossing with other genotypes. For this, seedlings of "Vaishnavi" and the normal mother variety PRC-1 were transplanted in alternate rows (1:2:: Vaishnavi: PRC-1) in the field at CIMAP Field Station, Pantnagar. The plants raised in this way were grown to flowering. Natural crossing between these parents was allowed to occur but simultaneously the florets of one parent was repeatedly dusted with the manually collected pollens of the other parent. Seeds were collected from individual plants of each parent and bulked, grown in nursery and later transplanted in field during 1993–94 in isolation blocks (to prevent outcrossing between the two classes of $F_1$s the total number of plants (supposed to be the $F_1$s) for "Vaishnavi" and PRC-1 being 700 and 300, respectively. Both classes of progenies were grown to flowering. It was interesting to note that all the "Vaishnavi" progenies, indicated that "Vaishnavi" is a recessive homozygous for all its plant traits and that both the hybrids received recessive alleles for the traits exclusively from "Vaishnavi" and the corresponding dominant alleles from PRC-1. These indications got an apparent support from the $F_1$ result of PRC-1. None of the 500 progenies of the latter exhibited any other phenotype than that of its own. The $F_2$ segregation study was made in two successive years (1995–96 and 1996–97) using the seeds ($F_2$s) of the two "Vaishnavi"-hybrids and of the selected 50 plants (supposed to be the $F_1$s) of PRC-1. The two $F_2$ populations of "Vaishnavi"-hybrid were sufficiently large to reveal that the PRC-1-type segregants were three fold more in frequency than the "Vaishnavi" type segregants. Thus, the $F_1$ results suggesting the homozygous recessivity in "Vaishnavi" for all the plant traits, could be confirmed by the $F_2$ results (Table. 3). In regard to the segregation study in $F_2$ families of PRC-1, unexpectedly all but four families with distinct segregation and analysable populations (86 to 248 plants), had no analysable populations (15 to 20 plants) and hence, did not reveal segregation results. The segregation results of the four analysable families were completely consistent with the results, we obtained for the $F_1$ and $F_2$ segregations for two "Vaishnavi" hybrids. In all the four hybrids, the genetic ratio clearly expected on account on Mendelian monogenic inheritance of 3:1 segregation and the complete homozygous recessivity in "Vaishnavi" for all the plant traits (Table. 4).

Stability Productivity and Quality Analysis:

"Vaishnavi" was assessed for its morpho-physiological fitnesses against the existing varieties/genetic stock (PRC-1, Trishna and Pantnagar Local) in preliminary yield trial (PYT) during 1993–97 using the Vaishnavi's selfed seeds in bulk. The per hectare/harvest oil yield in "Vaishnavi" in 165.4 kg as against 58.6 to 78.3 kg of the three control genotypes (PRC-1, Trishna and Pantnagar Local) (Table. 4). what was more axiomatically important that genotype Vaishnavi, despite its selfing, did not reveal any inbreeding depression for morpho-metric traits in its selfed progenies used in the PYT.

Essential oil samples, prepared from "Vaishnavi" and the mentioned three control genotypes were examined by gas chromatography (GC). The geraniol content in "Vaishnavi", though at par with that of Trishna, is higher than that of PRC-1 as well as Pantnagar Local (78–82% against 75–80% of the latter two genotypes) consistent with the preliminary yield results were the results from the pilot scale trial over the genotypes, which we conducted during 1998–99 at CIMAP Field Station, Pantnagar, the corresponding yield data being 164.7 kg/ha/harvest in "Vaishnavi" against 57.6 to 80.7 kg of the mentioned three control genotypes. The estimated geraniol yield/ha/harvest in "Vaishnavi" was 128.5 to 135.0 against 43.2 to 64.6 kg of the three control genotypes (Table. 2).

Chromosomal Analysis:

Efforts were made to confirm the apparently unique morpho-physiological features, especially the changed mating system (self pollinating habit against the cross pollinating habit of the normal plants) in "Vaishnavi" by chromosomal study. For this a thorough analysis of its meiotic chromosomes in the pollen mother cells (PMCs) was made. Our repeated chromosomal counts in PMCs revealed that "Vaishnavi", though it is largely distinct from the normal plants for morpho-physiological plant attributes, nevertheless it possesses the same chromosome number (2n=2x=20) as in the normal plants. It was possible to consider that this new genotype is the result of induced variations at genic level but not the result of induced amplification in chromosome number. In considering the fact that we recovered the novel genotype "Vaishnavi", apart from recovering the other macro-variants like chlorophyll variants and the variants with high somatic reproducibility (highly tillered variants) in high frequency as the progenies only from the burnt progenitors (the original burnt gene pool) but not from the normal plants, it clearly stands that it is the crop-burning temperature which induced heritable changes in the present material and resulted in the development of the novel mutant "Vaishnavi". Accordingly, it is possible to conclude that crop-burning temperature would be a potent physical mutagen for at least the present hardy and high temperature tolerant crop palmarosa.

Further, the results of genetic analysis of the reciprocal hybrids (Vaishnavi ♀×PRC-1♂ and PRC-1♀×Vaishnavi ♂) as well as the selfed progenies of Vashnavi clearly demonstrated that several desirable gene loci in Vaishnavi transmit en block from one generation to the next without undergoing any intergenic recombination either via selfing or, outcrossing. It appears likely that several linked loci have simultaneously been mutated in the progenitor (palmarosa cv. PRC-1) to give rise to the origin of the novel mutant "Vaishnavi".

Mutagenic Effect of Crop-Burning:
(i) Adduction of Hypothesis:

In order to further ascertaining the effect of crop-burning the applicants considered the hypothesis that if the high temperature has indeed been the mutagenic function it must repeat this function in other palmarosa homozygous genotype apart from the present material (heterozygous Population cultivar PRC-1). In this regard, the applicants developed a new plant "Vaishnavi" (a genotype homozygous for all the morphological traits owing its self-pollinating habit).

(ii) Results

A total of 200 healthy plants of Vaishnavi was raised in an isolated block measuring 9 m×4 m in size, sufficient for accommodating the plants with 60 cm×30 cm spacing for each plant. The control population block containing the same number of plants of Vaishnavi was raised in a contiguous block. Crop-burning was given when the plants were two years old (during 1995-'96) in almost the similar way as described earlier, but with one modification of providing a thin layer of dry lemongrass straw over the experimental plants to ensure uniform burning. We collected seeds from 50 randomly selected burnt plants, as they matured after suitable rejuvenation and flowering. Their bulked seeds were grown during 1996-'97 in progeny beds as $M_1$ generation. The $M_1$ population comprised 3,000 plants. The seeds from a total of 30 randomly selected $M_1$ plants were collected separately and grown in progeny blocks as $M_2$ generation during 1997-'98. The population size in the $M_2$ families ranged from 148 to 266. The corresponding novel variations, recorded in $M_1$ and $M_2$ are shown in FIG. 2. The $M_1$ plants, with rare exceptions of showing an extra-tall (245.2 cm against the general height of 226.6 cm in $M_1$ and 227.0 cm in the control plants and an extra-dwarf (40.3 cm) lethal albino plant as shown in FIGS. 2B & C, were morphologically identical with the control (unburned) plants. Of the two exceptional variants the extra-tall variant could be confirmed as the result of induction of a rare dominant mutation at the locus for plant height in Vaishnavi by studying its segregation pattern in the progeny (Tall: Dwarf:: 227:78; $X^2$, df=0.10 with P value 80 to 90). On the other hand, the other rare variant appeared to be the result of drastic chromosomal changes like large chromosomal aberration(s), which might have led to its lethality. Mutation frequency in $M_2$ generation was estimated at both $M_1$ plant bases (i.e. f=No. of segregating $M_2$ families/Total no. of $M_1$ plants×100) and $M_2$ seedling and plant bases. Surprisingly, mutation frequency was much high, compared to our earlier experiment with PRC-1. It varied from 2.10 to 10.715 at $M_2$ seedling and plant bases and 20.60 to 68.40% at the $M_1$ plant bases. It was evident that chlorophyll variations were much frequent than the other visible mutations, contributing 90.3% of the total variations induced. All the chlorophyll variants, except the mentioned one that had immediate $M_1$ expressivity as Albino-type and $M_1$-lethality, were of identical type in the form of "Zebra-cuts" as shown in FIG. 2A. The other amazing part of this study concerned the recovery of two classes of visible (viable) macro-variants: one of multi-branched inflorescence type comprising 5 plants and the other of morpho-physiologically much up-graded form comprising only 2 plants as shown in FIGS. 2D&E. Both the classes of plants were much dwarf (65.6 cm against 227.0 cm of Vaishnavi).

In considering these results of significant variations of progenies derived from the burnt progenitors and of absence of variations in the control (unburned) population, it could be ascertained that the high temperature of function, that could be deployed in genetically improving the hardy temperature-tolerant crop like palmarosa.

Statement of Distinction

As evident from the morphology, "Vaishnavi" is distinct form its mother variety PRC-1 as well as the other existing variety/genetic stock. The mentioned very shy stigma, not coming out of the glumes of the floret in spikelet (cleistogamous habit) "Vaishnavi" which leads to prevent the cross pollination, is a major "morphological marker" for identifying its self pollinating habit. The morphological peculiarities like almost awnless spikelets and robust size in inflorescence coupled with arrangement of spikelets on rachilla (branches of rachis) in clusters are also other important "markers" to identify Vaishnavi from all the existing genotypes of palmarosa. The high potentiality in setting seeds almost entirely through self pollination, high per se oil content potential and high biomass and oil productivity are the major "markers" for the prognosis of its physiological fitness.

The genotype of the plant, though diploid as other normal plants with chromosome number $2n=2x=20$, is unique to other normal varieties. All the desirable plant traits in Vaishnavi, besides being in true-bred (recessive homozygous) condition, transmit en block from one generation to the next without separating from each other through recombination, in view of their possible tight linkage among themselves. Such genotypic status of Vaishnavi leads it to offer a guarantee for its sustained advancement in productivity.

The novelty of the invention lies in the fact is that Vaishnavi, apart from being the first example of self pollinated variant with outstanding morpho-physiological Witnesses, is the first example in higher plant, which has raised the possibility that crop-burning temperature may be a potent physical mutagen in inducing novel variations in temperature tolerant higher plants, at least the present one (palmarosa) and hence, may prove as a potent substitute of chemical and other physical mutagens, which as generally known, are often associated with much risk and human hazards.

TABLE 1

Mean performances[1] of the genotype "Vaishnavi" and other existing three standard cultivars in Preliminary yield trial conducted during (1993–97) at Field Station, Pantnagar. (Plot Size: 6 m × 3 m accomodating 100 plants, spaced at 60 cm × 30 cm spacing).

| | Varieties/Strain | | | | |
|---|---|---|---|---|---|
| Characters | PRC-1 | Trishna | Pantnagar local | Vaishnavi | C.D (5%) |
| Plant height (cm) | 242.60 | 235.70 | 240.10 | 230.50 | 5.10 |
| No. of tillers per plant | 35.30 | 32.50 | 30.20 | 44.50 | 7.21 |
| Leaf length (cm) | 32.70 | 31.50 | 30.30 | 30.60 | 3.40 |
| Leaf Width (cm) | 1.64 | 1.62 | 1.58 | 1.80 | 0.10 |
| Herbage weight per plant (g) | 378.36 | 367.52 | 310.70 | 532.66 | 15.25 |
| Length of inflorescence (cm) | 25.67 | 25.50 | 25.21 | 25.30 | 0.80 |
| Length of internodes between spikelets (cm) | 0.70 | 0.65 | 0.63 | 1.60 | 0.56 |
| Number of rachilla per inflorescence | 7 | 6 | 6 | 13 | 3.0 |
| Number of spikelets per rachilla | 16 | 15 | 12 | 20 | 3.60 |
| Number of florets per spikelet | 5 | 4 | 3 | 7 | 1.63 |
| Number of florets per inflorescence | 560 | 360 | 216 | 1820 | 25.45 |
| Length of spikelet (mm) | 3.5 | 3.4 | 3.2 | 3.1 | 0.45 |
| Fresh weight of single inflorescence (g) | 5.30 | 5.15 | 5.00 | 7.10 | 3.38 |
| Inflorescence: Stem (w/w) ratio | 0.98 | 0.84 | 0.94 | 146 | 0.15 |
| Herbage yield/ha/yr/harvest (q) | 140.70 | 139.50 | 121.30 | 208.50 | 15.62 |
| Oil content (%) | 0.60 | 0.60 | 0.50 | 0.80 | 0.12 |
| Total oil yield per plant (g) | 3.53 | 2.39 | 1.55 | 6.10 | 2.65 |
| Oil yield/ha/harvest (kg) | 82.5 | 78.3 | 58.6 | 165.4 | 7.80 |
| Seed yield/plant (g): CPS[2]: | 22.40 | 20.51 | 16.30 | 0 | 5.10 |
| SPS[3] | 0 | 0 | 0 | 73.42 | — |
| Seed yield/ha (q) | 8 | 7.8 | 5.7 | 25.0 | 6.25 |
| Pollen fertility (%) | 88.70 | 72.52 | 80.42 | 86.76 | 4.32 |

[1]Average over 3 years (1994–97)
[2]CPS = cross pollinated seeds
[3]SPS = self pollinated seeds

TABLE 2

Comparative performances of the cleistogamous inbreeder (Vaishnavi) and other existing three standard cultivars in Plot-scale trial conducted during (1997–99) at Field Station, Pantnagar (Plot Size: 16 m × 5 m accomodating 444 plants spaced at 60 cm × 30 cm spacing).

| Varieties/ Strain | Plant height (cm) | Herbage yield/ha/yr/ harvest (q) | Oil content (%) | Oil yield/harvest[1] (kg) | Geraniol content (%) | Estimated Geraniol yield/ha/yr/ harvest (kg) | Seed yield/ (q) |
|---|---|---|---|---|---|---|---|
| PRC-1 | 240.70 | 138.70 | 0.60 | 80.7 | 75–80 | 60.5–64.6 | 7.8 |
| Trishna | 234.80 | 137.50 | 0.60 | 77.8 | 78–82 | 60.7–63.8 | 7.7 |
| Pantnagar Local | 237.60 | 120.40 | 0.50 | 57.6 | 75–78 | 43.2–44.9 | 5.5 |
| Vaishnavi | 228.40 | 207.80 | 0.80 | 164.7 | 78–82 | 128.5–135.0 | 24.3[2] |
| C.D (5%) | 4.95 | 15.50 | 0.11 | 7.62 | — | — | 6.20 |

[1]Average over three successive harvests during summer, autumn and winter.
[2]Self pollinated seeds.

TABLE 3

Segregation for "Vaishnavi" type segregants the $F_2$ populations of two VaishnaviE × PRC- II˝ crosses of palmarosa.

| | Phenotypes of $F_2$ progeny | | $X^2$-value idf | |
|---|---|---|---|---|
| Cross No. | PRC-1 type Normal plants (P) | "Vaishnavi" type variants (V) | (assuming P:V::3:1) | P-Values |
| 1. | 256 | 90 | 0.30 | 50–70 |
| 2. | 224 | 81 | 0.40 | 30–50 |

TABLE 4

Segregation for "Vaishhavi" type segregants in the $F_2$ populations of five PRC-1E × VaishnaviI˝ crosses of palmarosa.

| | Phenotypes of $F_2$ progeny | | $X^2$-value idf | |
|---|---|---|---|---|
| Cross No. | PRC-1 type Normal plants (P) | "Vaishnavi" type variants (V) | (assuming P:V::3:1) | P-Values |
| 8 | 75 | 28 | 0.30 | 50–70 |
| 9 | 77 | 30 | 0.53 | 50–70 |
| 16 | 185 | 69 | 0.63 | 30–50 |
| 28 | 68 | 18 | 0.76 | 30–50 |

What is claimed is:

1. A high yielding, stable and self-pollinated plant *Cymbopogon martinii*, known as seed deposit accession no. NCIMB 41154 with the NCIMB Ltd., 23 St Machar Drive, Aberdeen, AB24 3RY, Scotland and christened as 'Vaishnavi', belonging to the family Poaceae and having the following characteristics:

(a) self-pollinated genotype having no inbreeding depression;
   (b) having cleistogamous stigma that does not come out of glumes of the florets and hence prevents out-crossing;
   (c) florets ranging between 1780 to 1840 arranged in clusters on rachis;
   (d) recessive homozygous (true-bred) for all its morpho-physiological traits transmitting the said traits en block from its one generation to the next generation without undergoing genetic recombination between traits;
   (e) inflorescence: stem (w/w) ratio ranging between 1.40 to 1.50;
   (f) oil content ranging between 0.75 to 0.80%;
   (g) seed yield of at least 24.3 quintals per hectare;
   (h) oil yield of at least 164.7 kg per hectare;
   (i) geraniol yield of at least 135.0 kg per hectare; and
   (j) oil constituents comprising geraniol of at least 78% and geraniol acetate of at least 8% and the rest being unidentified fractions in the essential oil all totaling to 100% at different stages of growth.

2. The seeds of the plant of claim 1 deposited at the NCIMB Ltd., 23 St Machar Drive, Aberdeen, AB24 3RY, Scotland having accession no. NCIMB 41154.

* * * * *